United States Patent
Hassler

(10) Patent No.: US 8,758,786 B2
(45) Date of Patent: Jun. 24, 2014

(54) PREPARATION FOR REDUCING AND/OR PREVENTING BODY FAT AND RESPECTIVE USES, IN PARTICULAR TOGETHER WITH A DRESSING MATERIAL

(76) Inventor: Gerard Hassler, Oberaegeri (CH)

( * ) Notice: Subject to any disclaimer, the term of this patent is extended or adjusted under 35 U.S.C. 154(b) by 394 days.

(21) Appl. No.: 12/439,220

(22) PCT Filed: Aug. 28, 2007

(86) PCT No.: PCT/EP2007/007508
§ 371 (c)(1),
(2), (4) Date: Jul. 2, 2009

(87) PCT Pub. No.: WO2008/025511
PCT Pub. Date: Mar. 6, 2008

(65) Prior Publication Data
US 2010/0015190 A1    Jan. 21, 2010

Related U.S. Application Data

(60) Provisional application No. 60/840,779, filed on Aug. 28, 2006.

(30) Foreign Application Priority Data

Sep. 7, 2006  (DE) .......................... 10 2006 042 113

(51) Int. Cl.
*A61K 31/675*   (2006.01)
*A61P 3/04*     (2006.01)

(52) U.S. Cl.
USPC ............. 424/402; 424/94.1; 424/445; 514/81

(58) Field of Classification Search
USPC ............................ 424/402, 94.1, 445; 514/81
See application file for complete search history.

(56) References Cited

U.S. PATENT DOCUMENTS

| | | | |
|---|---|---|---|
| 2004/0143026 A1* | 7/2004 | Shah .......................... | 514/772.3 |
| 2004/0176448 A1* | 9/2004 | Blatt et al. ...................... | 514/547 |
| 2005/0239077 A1* | 10/2005 | Adam et al. ....................... | 435/6 |
| 2006/0153926 A1* | 7/2006 | Bascom et al. ................ | 424/523 |

FOREIGN PATENT DOCUMENTS

| | | |
|---|---|---|
| FR | 2 694 195 | 2/1994 |
| FR | 2 797 765 | 3/2001 |
| GB | 2 305 603 | 4/1997 |
| WO | WO 00/44346 * | 8/2000 |

* cited by examiner

*Primary Examiner* — Anoop Singh
*Assistant Examiner* — Anna Falkowitz
(74) *Attorney, Agent, or Firm* — Saliwanchik, Lloyd & Eisenschenk

(57) ABSTRACT

The present invention relates to human metabolism, in particular fat reduction and a cosmetic and pharmaceutical formulation, as well as respective uses in particular together with a dressing material according to the invention.

13 Claims, 13 Drawing Sheets

A B

PREPARATION FOR REDUCING AND/OR PREVENTING BODY FAT AND RESPECTIVE USES, IN PARTICULAR TOGETHER WITH A DRESSING MATERIAL

CROSS-REFERENCE TO A RELATED APPLICATION

This application is a National Stage Application of International Application Number PCT/EP2007/007508, filed Aug. 28, 2007; which claims the benefit of U.S. Provisional Application Ser. No. 60/840,779, filed Aug. 28, 2006, and also claims priority to German Application No. 10 2006 042 113.2, filed Sep. 7, 2006; all of which are incorporated herein by reference in their entirety.

FIELD OF THE INVENTION

The present invention relates to human metabolism, in particular fat reduction and a cosmetic and pharmaceutical formulation, as well as respective uses in particular together with a dressing material according to the invention. For the purposes of the present invention, all references as cited herein are included by reference in their entireties.

BACKGROUND OF THE INVENTION

Excess body fat can detract from personal appearance, reduce athletic performance, and even result in risks to health. Human health problems associated with excess body fat include diabetes and cardiovascular disease. In many situations, excess body fat can be reduced by increasing physical activity, reducing caloric intake, or both. Nevertheless, these traditional approaches are often impractical or insufficient, for example due to physical injury or metabolic disorder. In addition, methods based solely on exercise or diet cannot be targeted effectively to achieve fat loss in specific locations on the body.

An alternative method of reducing body fat is stimulating metabolic rate by administration of pharmacologically active agents. Examples of drugs used to stimulate metabolism are hormones, e.g., human growth hormone or insulin-like growth factor, and stimulants, e.g., ephedrine or caffeine. Disadvantages of using drugs to reduce body fat include the need for medical supervision and the risk of unwanted side effects.

GB 2305603 discloses topical gels containing a volatile and/or absorbable component to cool the skin thereby initiating localised thermogenesis but preventing localised temperature equilibration. This localised thermogenesis leads to removal of the fat deposits via their metabolism. The treated skin may be covered with fabric such as a jump-suit. Exemplified compositions contains 0.9% carbomer, 0.2% preservative, 0.2% sodium EDTA, 2.53% menthol, 1.0% camphor, 20.00% ethanol, 0.001% FD & C Blue, 0.4% triethanolamine, 0.2% d-panthenol, 0.5% hyaluronic acid and made up to 100% with water. The concept of GB 2305603 is thus to utilise this phenomenon of thermogenesis, and to activate it locally, by preparing a composition which can be controllably applied to the excess fatty areas of the body, without allowing the body to overcome the "cold" effect in the treated area. In other words, the composition is so formed that the body surface temperature is allowed to drop locally at the treated area, by only a small amount for example between a half and four degrees. GB 2305603 tries to reduce body fat by an "externally applied" effect.

DE 2405900 describes a weight reduction preparation to be applied locally using a bandage or wrap having an absorption capacity of about 35%, wherein the preparation consists of 51% alcohol (96%), 30% camomile, 4% menthol, 4% camphor, 3% sodium chloride, 2% calcium chloride, and 6% potassium chloride in a saturated solution to be applied. DE 2405900 also tries to reduce local body fat by an "externally applied" effect.

Finally WO 00/44346 discloses compositions and methods for controlled lowering of skin temperature of a human subject. The method includes providing a cooling solution comprising about 60-90% water, about 40-10% alcohol, 0.02-2.0% menthol, and 0.02-2.0% camphor; contacting the cooling solution with a region of the skin of the subject for 10 to 60 minutes, thereby cooling the skin. This controlled skin cooling stimulates a localized thermal response. Stimulation of the thermal response at appropriate time intervals can be used to achieve localized fat reduction or to reduce localized inflammation. Thus, WO 00/44346 also tries to reduce local body fat by an "externally applied" effect.

Although there has been a long-lasting attempt to provide for an effective and comfortable way to reduce local body fat, as can be taken from the above references, still an effective preparation is lacking that effectively reduces local body fat, and at the same time has an acceptable compliance for the user. Another important aspect is the safety of the product in order to allow its use, for example, in a pediatric environment.

Pieces of clothing are usually formed by woven or non-woven fabrics and are put on in order to enwrap human body parts. Thereby, a tubular structure is provided for each body part, which is adapted to the size of the respective body part. The tubular fabric wrap has an essentially axial extension, into which the body part extends, and an essentially radial extension around said body part. For a good fit to the body part the fabric wrap is endlessly closed in its perimeter so that a kind of a tunnel-like structure is formed. It is common that pieces of clothing—e.g. provided with an elastomer material—have certain kind of elasticity and are dimensioned in a way that they fit the shape of said body part adapting it in its perimeter.

In recent years in particular in the field of sports technology new clothing systems have been developed which are supposed to ensure an optimum heat and liquid dissipation from the skin to the outside via the piece of clothing. Furthermore, these so-called "breathable" materials have the job to repel liquids, such as rain. With these systems it is acted on the assumption that a higher performance of the human body can be achieved with sufficient heat dissipation and preventing intense accumulation of wetness on the skin. Above all, these breathable pieces of clothing are supposed to prevent the body from cooling off as soon as the workout phase is over.

It is common knowledge to cool body parts by applying cooling agents or cooling gels to the respective regions of the skin in order to reduce or prevent injuries of body parts, such as muscles or joints. If necessary, the region which the cooling cream or cooling lotion has been applied to can be covered with a compress or a dressing material.

Furthermore, in particular in sweaty sports, such as tennis, it is common to wear arm or headbands, which are supposed to absorb endogenous liquids, such as sweat, so that these liquids cannot reach the body regions required for the sport.

It is a first object of the invention to provide a preparation that effectively reduces local body fat, and at the same time has an acceptable safety and compliance for the user.

It is a second object of the invention to provide for a piece of clothing for a human body part with extended functionality, in particular by which the performance of the human body can be enhanced or a metabolic activity in a particular region of the body can be stimulated.

Other objects of the present invention will become apparent to the person of skill when reading the following specification, examples, claims and figures of the present invention.

SUMMARY OF THE INVENTION

In a first aspect thereof, the invention features a physiologically acceptable composition, comprising between about 5-15% alcohol, between about 80-90% water, between about 0.1-2% menthol and/or camphor, and between about 0.1-2% coenzyme A and/or between about 0.1-2% carnitine, and/or between about 0.1-2% caffeine. The amount of water can be about 75% to about 90%, while the amount of alcohol is about 25% to about 10%. In some embodiments, the preferred amount of water is about 84% and the amount of alcohol is about 15%.

The alcohol can be ethanol, isopropanol, or a mixture thereof. In general, all physiologically acceptable alcohols can be used.

In some embodiments, a preferred composition further comprises a skin conditioning agent. In some embodiments, a preferred skin conditioning agent is an emollient. Said emollient is preferably PEG-7 glyceryl cocoate (e.g. Cetiol HE; Henkel).

Further preferred is a composition according to the invention, consisting of about 18% ethanol, about 81.5% water, about 0.1% menthol, about 0.1% camphor, about 0.1% coenzyme A, about 0.1% carnitine, and about 0.1% caffeine.

A further aspect of the present invention relates to a cosmetic preparation, comprising a composition according to the present invention.

A further aspect of the present invention relates to a method for controlled lowering of skin temperature of a human subject, comprising: providing a composition according to the present invention, and contacting the cooling solution with a region of the skin of the subject for 10 to 60 minutes, thereby cooling the skin.

In a preferred embodiment, the composition is contacted with the skin for 5-240, preferably 15-90 minutes, more preferably for 30-60 minutes for fat reduction. Further preferred is a method according to the present invention, wherein the composition is contacted with the region of the skin by a woven or nonwoven fabric wrap. Said fabric wrap can be an elastic cotton crepe bandage, brace or vest. For use on arms, a bandage width of about 5 to 12 cm is suitable, with a width of about 10-20 cm being preferred. For use on the legs and body, a bandage width of about 10-20 cm is suitable, with about 20 cm being preferred.

In yet another preferred embodiment of the method according to the present invention, the controlled reduction of skin temperature in the region of skin contacted with the composition is a reduction of 3° C. to 12° C. More preferred is a method according to the present invention, wherein the controlled reduction of skin temperature in the region of skin contacted with the cooling solution is a reduction of about 8° C.

A further aspect of the present invention then relates to a cosmetic treatment, comprising a method according to the present invention. Preferred is a treatment, wherein the cosmetic treatment is against local body fat. Most preferred is a treatment of cellulitis.

Yet a further aspect of the present invention then relates to a method for preventing or reducing systemic and/or local body fat, comprising a method according to the present invention. Most preferred is a method, wherein said treatment is for a pediatric form.

Yet a further aspect of the present invention then relates to a method for preventing or treating systemic and/or local obesity, comprising a method according to the present invention. Most preferred is a method, wherein said treatment is for a pediatric form.

Yet a further aspect of the present invention then relates to a method for preventing or treating obesity and obesity related diseases, comprising a method according to the present invention. Most preferred is a method, wherein said treatment is for a pediatric form.

In another aspect of the present invention a composition according to the present invention is used for the production of a pharmaceutical composition for the treatment of a disease as above. In one embodiment, the disease is type II diabetes, particularly type II diabetes in children.

The controlled lowering of skin temperature in the region of skin contacted with the composition can be a decrease of 3° C. to 12° C., with respect to the pretreatment skin temperature. Preferably, the decrease is 4° C. to 8° C., more preferably 5° C. to 7° C., and most preferably about 6° C., when the skin treatment is used for fat reduction. This decrease is produced over a period of 4 minutes to 15 minutes.

The invention also provides a cooling solution concentrate that can be diluted with water to obtain a cooling solution suitable for contacting with the skin in the method of the invention. The concentrate contains 80% to 95% alcohol, wherein the alcohol is ethanol, isopropanol, or a mixture thereof; 0.1% to 10% menthol, 0.1% to 5% camphor, 0.1% to 5% coenzyme A and/or 0.1% to 5% carnitine, and/or 0.1% to 5% caffeine.

A preferred embodiment of the concentrate contains: about 60% ethanol; about 36% isopropanol; about 0.8% menthol; about 0.8% camphor; 0.8% coenzyme A; 0.8% carnitine; and 0.8% caffeine. Optionally, the concentrate contains about 1% to 4% water. The concentrate also can contain a skin conditioning agent, for example an emollient. A suitable emollient is PEG-7 glyceryl cocoate, and a suitable amount of PEG-7 glyceryl cocoate in the concentrate is about 5.5% (and less water).

Unless otherwise defined, all technical and scientific terms used herein have the same meaning as commonly understood by one of ordinary skill in the art to which this invention belongs. In case of conflict, the present application, including definitions will control. All publications, patent applications, patents, and other references mentioned herein are incorporated by reference.

Accordingly, the fabric wrap forming said piece of clothing is provided with an elastic extensibility, which is a multiple times higher in the radial extension than in the axial extension of said fabric wrap. Furthermore, according to the present invention said fabric wrap has to be formed particularly from untreated cotton. Finally, said fabric wrap, when spread out, has a mass of about 56 to 106 g per m$^2$, so that it can carry an exogenous liquid, and said liquid can get into direct contact with said body part. The piece of clothing with the above-mentioned features according to the present invention exhibited surprising characteristics in terms of absorbing and carrying exogenous liquids. On the one hand, the piece of clothing according to the present invention allows the liquid to get close, in particular get into contact with the skin of said body part in such a way that the region of said body part can be cooled by evaporation of the liquid. On the other hand, the special design of said piece of clothing ensures that the fabric wrap can be passed by the surrounding air so that the heat of evaporation and the moisture in the region of said body part can be removed. It was shown that the use of specific liquids, which contain for example alcohol and caffeine, is accompanied by constant cooling, which enhances the performance of a human being significantly. Surprisingly, it also appeared that the human organism causes a metabolic stimulation, in particular burning of fat in the region of said body part. The piece of clothing according to the present invention exhibited optimum characteristics in terms of carrying such liquids in order to cause the desired cooling effects and/or metabolic activities.

WO 00/44346 discloses compositions and methods for the controlled reduction of skin temperature in a human subject. The method includes the administration of a cooling solution comprising about 60-90% water, about 40-10% alcohol, 0.02-2% menthol, and 0.02-2% camphor, wherein said cooling solution is brought in contact with a region of the skin of said subject for 10 to 60 min, thereby cooling the skin. This controlled cooling of the skin stimulates a local temperature response. The stimulation of said temperature response for appropriate time periods can be used to achieve local degradation of fat or to reduce local inflammations.

The extensibility of the fabric in radial extension can be at least 2 times, at least 4 times, at least 6 times, or up to 10 or 15 times higher than that in axial extension. Preferably, the fabric wrap is barely extensible axially, but only in radial extension.

In a preferred embodiment of the fabric wrap according to the present invention, said fabric wrap is formed by at least one fabric layer, preferably two fabric layers put on top of each other, in particular attached to each other. The fabric layer consists of longitudinal threads, which run essentially in axial extension, and lateral threads, which run essentially along the perimeter of said fabric wrap. In order to maintain the desired a multiple times higher extensibility of the fabric wrap in radial extension, the longitudinal threads are essentially extended and not further extensible, wherein said lateral threads are non-extended and woven around said lateral threads. In particular, said lateral threads are wavy and/or curly in order to realize the extensibility by extension of the wavy and curly lateral threads. Preferably, the non-extension of the lateral threads is achieved by their torsion, wherein the lateral threads are woven in while being twisted relative to the extended thread axis. In a preferred embodiment said lateral and longitudinal threads consist of pure cotton.

Those threads that are called "chain" in the process of producing the fabric are to be regarded as lateral threads. Correspondingly, those threads that are called "pick" in the process of producing the fabric are the longitudinal threads.

In one embodiment of the present invention said longitudinal threads are always realized by one and the same kind of thread. Preferably, said one and the same kind of thread has a thread size of about 25 tex, wherein the unit "tex" corresponds to grams per 1000 m.

Preferably, said longitudinal thread of one and the same kind of thread is formed by a single thread.

Preferably, the number of said longitudinal threads per 10 cm of fabric wrap is 54+/−2.

In one embodiment of said fabric wrap with longitudinal and lateral threads according to the present invention at least two different kinds of thread are used for said lateral threads, in particular two different thread sizes. Herein, said lateral thread is bigger than the other, in particular has double the thread size of the other. In a preferred embodiment one lateral thread has a thread size of 25 tex, and the bigger one has a thread size of 50 tex. An especially suitable fabric wrap is provided when the smaller lateral thread is provided with a double thread structure, wherein two base threads are twisted longitudinally. Herein, the bigger thread is formed by a single thread.

Preferably, the thread number of one lateral thread, in particular the smaller lateral thread is 27 to 58 per 10 cm, wherein the thread size of the other lateral thread, in particular the bigger lateral thread is about 50 tex.

Preferably, the ratio of the smaller lateral thread and the bigger lateral thread is either 1:3 or 1:1.

In a preferred embodiment of the fabric wrap according to the present invention a third different kind of thread is used for the composition of said lateral threads. Said third kind of thread can have a thread size of 20 tex, wherein its thread number is about 4 per 10 cm.

The best results for the fabric wrap according to the present invention in terms of carrying liquids for cooling a body part or for stimulating fat burning in the region of said body part are achieved by a dressing material, such as a bandage, a suspensory bandage, or a compression, which is tailored to form a tubular, in particular tunnel-like structure. Suitable dressing strips can be obtained under the article description 40236049 or 40238075 from the company Karl Otto Braun KG in Wolfstein, Germany.

Preferably, said dressing strips have a width of about 20 cm. Said dressing strip is trimmed at a certain length in order to form a double layer material for producing said fabric wrap. Herein, adjoining lateral sides of the superposed dressing strips can be connected, particularly sewed with each other.

The piece of clothing according to the present invention can be an arm sleeve, a leg sleeve, a wrist sleeve, an elbow sleeve, a neckband, a fitting headdress, a vest, a dress, a t-shirt, gloves, stocking, and a chest cover, which is held in place by a neck sleeve via a single-piece junction.

Furthermore, the present invention relates to an assembly of several pieces of clothing according to the present invention. The pieces of clothing put on several body parts don't have to be connected with each other. However, they can be connected with each other by a piece of material, said piece of material being produced from the same material as said pieces of clothing.

Furthermore, the present invention relates to the use of a dressing material, such as the basis material of a bandage, a suspensory bandage, or a compression, as sold by the company Karl Otto Braun KG and as meant for wrapping a body part, such as an arm, a leg, a neck, a torso, or a combination thereof, as liquid carrier attached to said body part. Herein, said dressing material according to the present invention is formed into a tubular, in particular tunnel-like structure, closed in its perimeter, wherein said structure is endless in its perimeter. Said structure is used to be soaked with an exogenous liquid and to be carrying it in such manner that said liquid gets into direct contact with said body part.

Preferably, said liquid is a physiologically acceptable composition comprising between about 5-15% alcohol, between about 80-90% water, between about 0.1-2% menthol and/or camphor, and between about 0.1-2% coenzyme A, and/or between about 0.1-2% carnitine, and/or between about 0.1-2% caffeine. In a preferred embodiment, said composition comprises about 15% alcohol, about 84% water, about 0.2% menthol and 0.2% camphor, about 0.2% coenzyme A, about 0.2% carnitine, and about 0.2% caffeine.

In a preferred embodiment, said structure is formed by at least two, preferably exactly two superposed layers of dressing material, which are attached, in particular sewed, to each other via their rims.

It is particularly clear that the use of the dressing material as a liquid carrier can be realized in such manner that said piece of clothing is realized according to the piece of clothing.

Further advantages, properties, and features of the present invention become apparent by the following description of preferred embodiments of the present invention by means of the enclosed drawings, wherein Although methods and materials similar or equivalent to those described herein can be used in the practice of testing of the present invention, the preferred methods and materials are described below. The materials, methods, and examples are illustrative only and not intended to be limiting. Other features and advantages of the invention will be apparent from the detailed description, and from the claims.

DETAILED DESCRIPTION OF THE INVENTION

Controlled lowering of skin temperature according to the invention is useful for fat reduction, particularly fat reduction localized to one or more regions of the human body. Controlled lowering of skin temperature according to the invention is also useful for reduction of localized inflammation. The methods and compositions of the invention are safe and non-invasive.

Figure 1:
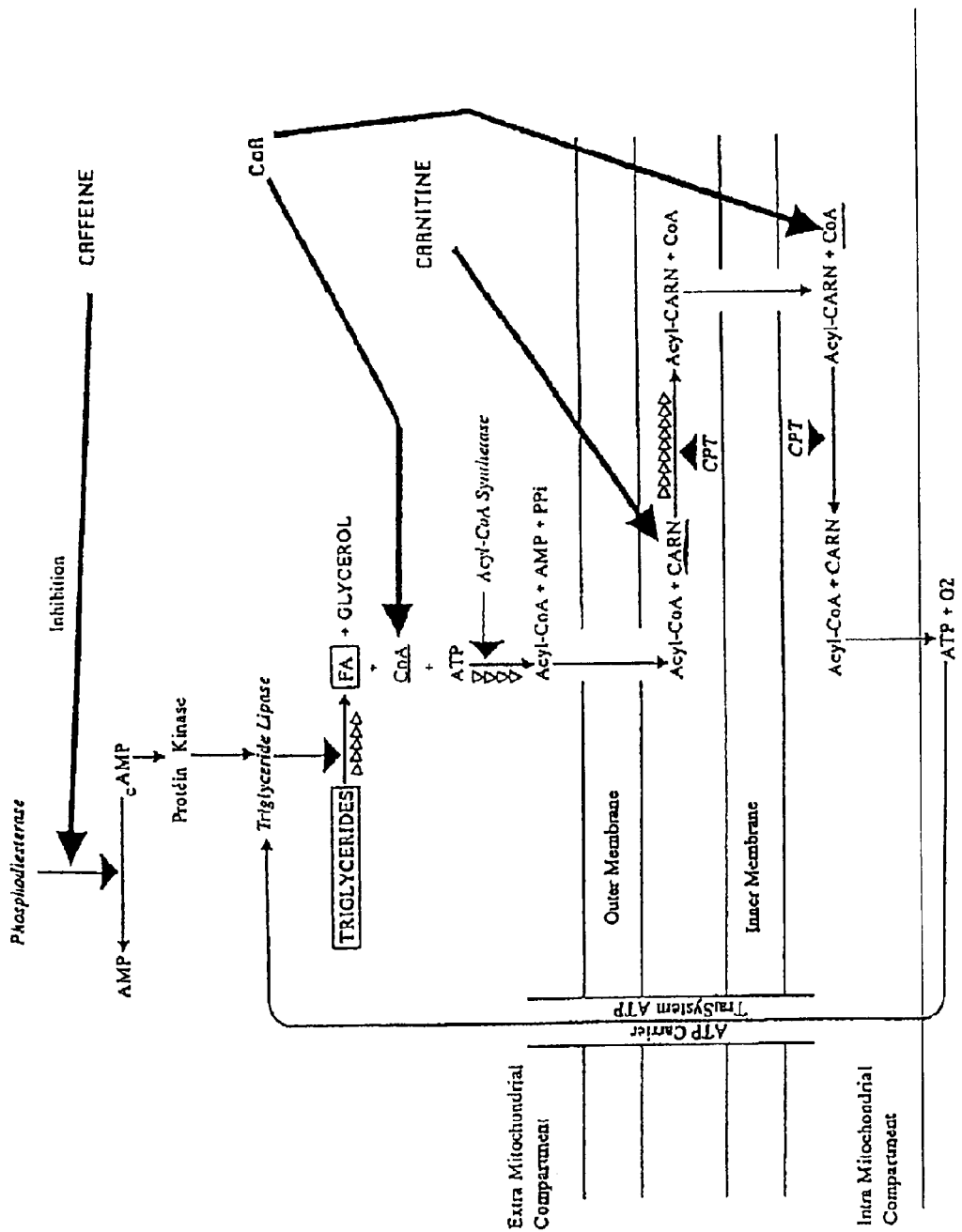
FIG. 1 is a schematic drawing showing the cellular triglyceride-related metabolism together with the effects of the active components of the composition of the invention. In particular, the roles of Coenzyme A, L-Carnitine and caffeine in activating lipolysis are shown. The addition of CoA and L-Carnitine allows the uptake and the destruction of free fatty acids to be increased. The resulting increase in ATP production in turn increases the efficiency of triglyceride lipase. Caffeine inhibits the degradation of AMPc, thus enhancing the breakdown of triglycerides. FA=free fatty acids; CoA=Coenzyme A; CARN=Carnitine; TGLipase=triglyceride lipase; CPT=carnitine palmitoyl tranferase. Small triangles indicate the displacement direction of the reactions.
Figure 2:
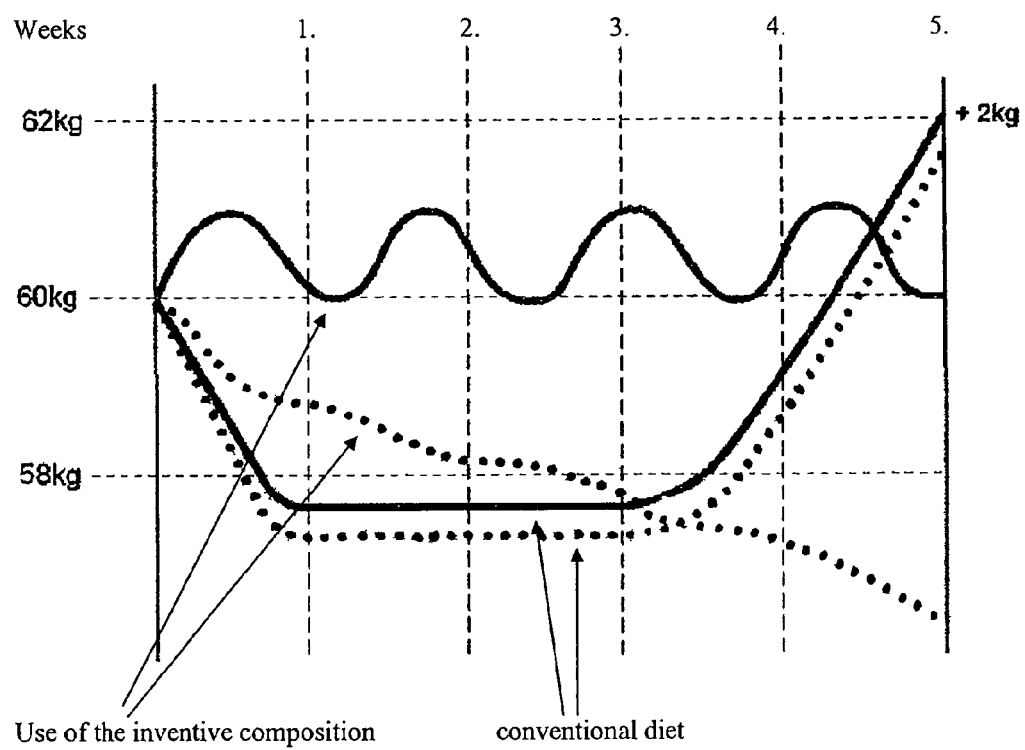
FIG. 2 is a graphical representation showing a comparison of weight loss according to a regular diet (dashed line), compared to a diet based on the composition of the invention (dashed line), together with the activity of the lipid metabolism in both cases (straight lines) according to example 1. The different treatments are indicated by the arrows.

As can be seen with reference to FIG. 1, the present composition, in addition to providing a cooling for fat reduction, contains amounts of coenzyme A, carnitine, and caffeine that (without wanting to be bound by theory) provide an "active" effect on the metabolism of fat in the cells of the body. This inventive concept stands in contrast to yet applied cooling solutions that merely provided a "passive" fat reduction through lowering of the temperature. Of course, the invention encompasses to use only one of the "active" components, nevertheless, the effect is most pronounced, if all three components are used.

Suitable rates of skin temperature decrease, and maintenance of suitably lowered skin temperatures, can be achieved with the methods and compositions of the invention, without skin temperature monitoring. If desired, however, skin temperature can be measured from time to time, or monitored continuously, using conventional devices and techniques.

Without intending to be bound by theory, it is believed that the skin temperature lowering results primarily from evaporation of the alcohol and water applied to the skin. Accordingly, the rate and extent of skin temperature lowering depends largely upon the water:alcohol ratio. Increasing the alcohol content accelerates and intensifies the cooling effect. The water:alcohol ratio can be adjusted, if necessary, to increase or decrease the rate and extent of cooling.

Such adjustment can be made by a person of ordinary skill in the art, without undue experimentation. This controlled skin cooling stimulates a localized thermal response, which requires energy provided by metabolism.

Stimulation of the thermal response at effective time intervals can be used to achieve localized fat reduction or to reduce localized inflammation. Furthermore, without intending to be bound by theory, it is also believed that caffeine, carnitine and coenzyme A have an additional effect to achieve localized fat reduction, and might even have a systemic effect.

Without intending to be bound by theory, it is also believed that mild vasodilation near the skin is stimulated by the menthol and camphor, and that this promotes the "spot reduction" of fat, when used in combination with the cooling provided by the alcohol/water mixture. The amount of menthol and camphor can be adjusted, as desired. Such adjustment can be made by a person of ordinary skill in the art, without undue experimentation.

In addition to stimulating vasodilation, the menthol and camphor display mild analgesic properties and antipruritic properties, cause a pleasant sensation when applied to the skin, and impart a pleasant odor to the solution. These sensual effects enhance the pleasurability of the skin cooling treatment. This increases the likelihood of regular use of the treatments, which maximizes achievement of the desired results.

Various alcohols can be used in the cooling solution. Ethanol (ethyl alcohol) and isopropanol (isopropyl alcohol) are preferred, because of their suitable evaporation rate, nontoxicity in topical application, and mild odor. Because their evaporation rates are similar, ethanol and isopropanol can be substituted for each other as the sole alcohol in the cooling solution. Alternatively, ethanol and isopropanol can be mixed in any ratio, to achieve the desired total alcohol content in the cooling solution. Some subjects prefer ethanol over isopropanol because of the difference in odor. Suitable water:alcohol ratios are described in the Summary of the Invention (above).

Because of its transdermal toxicity, methanol (methyl alcohol) is not suitable for use in the invention. Ethanol included in a cooling solution may contain small amounts of denaturing agents, i.e., agents used to render the ethanol unfit for human consumption.

If a denaturing agent is present, preferably it is not methanol.

Menthol and camphor are nontoxic when applied topically. Both compounds can be produced by well known methods and are commercially available in grades (purity) suitable for application to human skin. Amounts of menthol and camphor suitable for a cooling solution are described in the Summary of the Invention (above).

One or more skin conditioning agents can be included in the cooling solution. PEG-7 glyceryl cocoate, available commercially as Cetiol HE (Henkel), is preferred. Examples of other suitable skin conditioning agents are Estol EO3GC 3606 (Unichema), Fitester HE (Hispano Quimica), Glycerox HE (Croda), Hodag POE (7) GML (Calgene), Mazol 159 (PPG), Rewoderm ES 90 (Witco), Sterol LG 491 (Cesalpina), Tegosoft CG (Goldschmidt), Unimul HE (UPI), and Unitolate HE (UPI).

A cooling solution can be prepared initially to contain all components at a concentration desired for application to the skin according to the invention. For convenience, however, the cooling solution can be prepared, packaged, and transported as a concentrate, which is diluted with water prior to use. The components of a preferred concentrate are listed in Table 1.

TABLE 1

Concentrated Cooling Solution

| Component | Percentage | Weight | (grams) |
|---|---|---|---|
| Ethanol | 60 | 0 | 98.4 |
| Isopropanol | 30 | 6 | 50.2 |
| Water | 2 | 3 | 3.8 |
| Cetiol (PEG-7 glyceryl cocoate) | HE | 5.5 | 9.0 |
| Menthol | (crystal) | 0.8 | 1.3 |
| Camphor | 0.8 | 1.3 | 1 |
| Caffeine | 0.8 | | |
| Coenzyme A | 0.8 | | |
| Carnitine | 0.8 | | |

Prior to use, the concentrate defined in Table 1 is diluted. For example, for use in fat reduction, it can be diluted with 5 parts water to 1 part concentrate, to obtain a final water:alcohol ratio of about 85:15.

Variation in the final water:alcohol ration, e.g., for use in reducing inflammation, can be obtained by adjusting the dilution ration. For example, the concentrate defined in Table 1 can be diluted with 4 parts water to 1 part concentrate. Water need not be present in the concentrate. For convenience, however, it may be advantageous to include water in the concentrate.

This may enable the desired final concentrations of the various components to be obtained by using a dilution ratio based on whole numbers, e.g., Pure, 1:1, 1:2, 1:3, 1:4, 1:5, or 1:6 or 1:7 or 1:8 (concentrate:water).

To achieve controlled lowering of skin temperature, a film or layer of the cooling solution is contacted with a region of the skin for 5 to 240 minutes.

The necessary contact between the skin and the cooling solution can be accomplished in any of various ways.

Preferably, unhindered evaporative cooling takes place at the skin's surface throughout the skin cooling treatment, i.e., the period of 10 to 120 minutes when the solution is contacted with the skin.

During a skin cooling treatment, the solution can be intermittently poured or sprayed onto the treated region of skin. In preferred embodiments of the invention, a woven or non-woven fabric as described above is wrapped around a portion of the body and wetted with the cooling solution.

When a wetted fabric wrap is used, the initial wetting can be done before or after the wrap is placed on the body. A convenient and effective technique is to dip a cotton elastic crepe bandage into the solution, gently wring excess solution from the bandage, and then wrap the bandage onto the portion of the body to be treated.

Preferably, the bandage contains enough solution to feel wet, but not enough to result in dripping. As the solution evaporates during a skin cooling treatment, additional solution can be applied to the fabric by any convenient means, as necessary to maintain an optimal moisture content. During the skin cooling treatment, the person being treated can stand, sit or lie down, according to personal preference and comfort.

A "skin cooling treatment" is a single instance of contacting the solution with a region of the skin of the subject and maintaining the solution in contact with the region for 5 to 240 minutes, thereby cooling the skin.

Typically, multiple skin cooling treatments are applied at effective time intervals.

When skin cooling treatments are used to reduce body fat, preferably rewarming is allowed to occur naturally, e.g., over a period of about 15-60 minutes.

Preferably the methods and compositions of the invention are used in a series of skin cooling treatments. The intervals between treatments can vary. The optimal interval depends on whether the skin cooling treatments are being used to promote fat loss or to reduce inflammation.

For promoting fat loss, the interval between treatments is preferably between one week and 12 hours. More preferably, the interval is from 24 to 72 hours.

Figure 6:
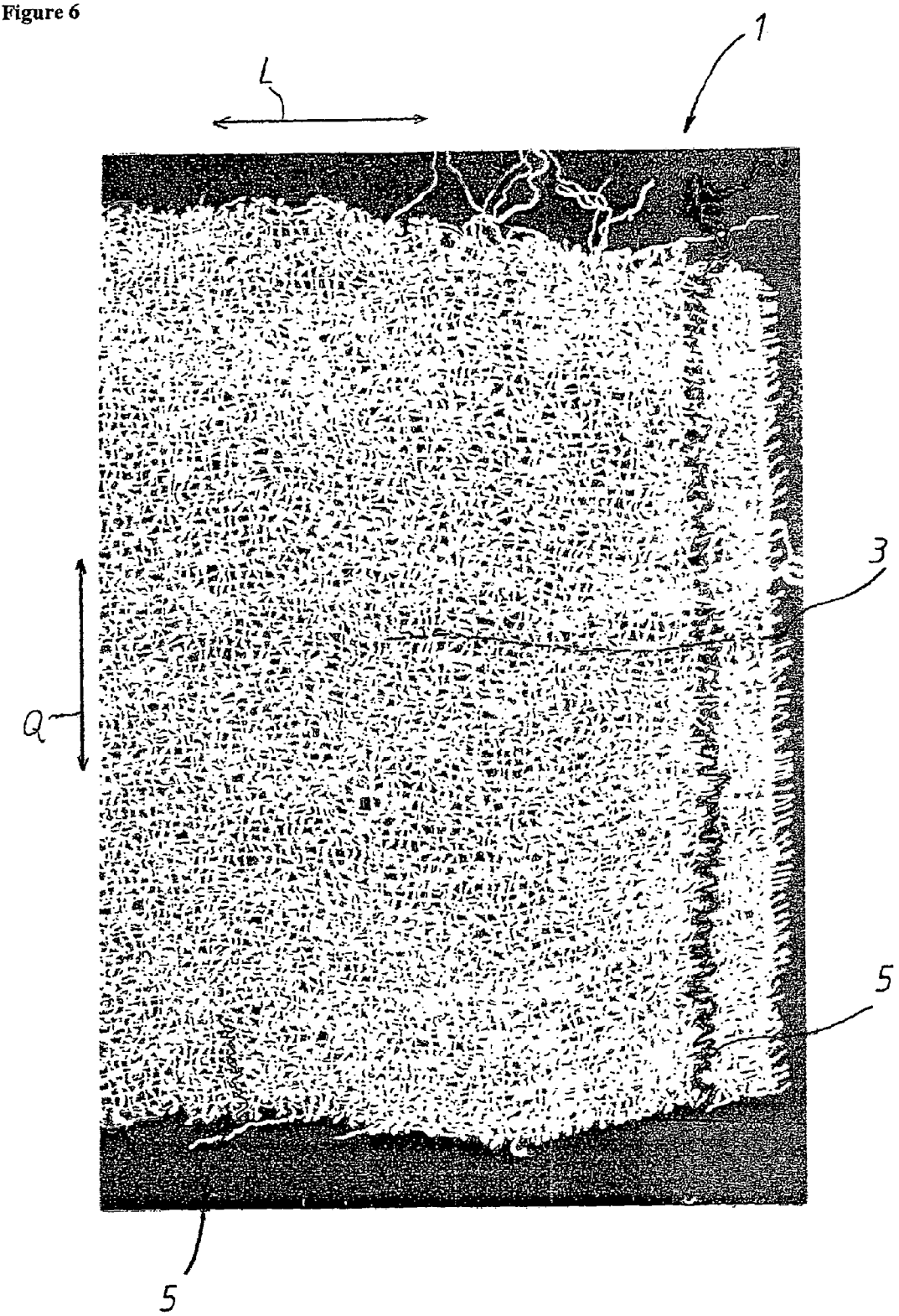
FIG. 6 shows a photographic top view of a dressing material for the piece of clothing according to the present invention, which is used as carrier of an exogenous liquid.

The base material for the piece of clothing according to the present invention is tagged with reference number 1 in FIG. 6. Base material 1 is a fabric for a dressing, which is produced by the company Karl Otto Braun KG. The fabric of base material 1 comprises as main components longitudinal threads 3, which are also called pick, and lateral threads 5, which are also called chain. Said longitudinal threads 3 are approximately parallel to each other and are essentially extended so that base material 1 does barely have any elasticity in the longitudinal direction L.

However, base material 1 has an a multiple times higher elastic extensibility in the lateral direction Q. During the extension of base material 1 in longitudinal direction, said lateral threads, which are parallely aligned, are moved away from each other depending on where the extension forces are effective in base material 1. The elastic extensibility of the fabric in the lateral direction Q is realized by the fact that the lateral threads 5 are non-extended when woven into the base material 1. As indicated in FIG. 6, the lateral threads 5 run curlily or wavily past the longitudinal threads 3 and are woven into base material 1. The wavy characteristic of the lateral threads 5 is particularly achieved by the fact that said lateral threads 5 are twisted prior or during being woven into the base material 1. By applying forces in lateral direction Q the inherent twist of the lateral threads 5 is removed, and the respective lateral threads 5 are extended. The extensibility of base material 1 is limited to the point when the respective lateral threads have reached the same complete extension as the longitudinal threads 3.

According to the present invention said base material 1 is used to produce a tubular fabric wrap with which the piece of clothing can be realized.

Figure 7:
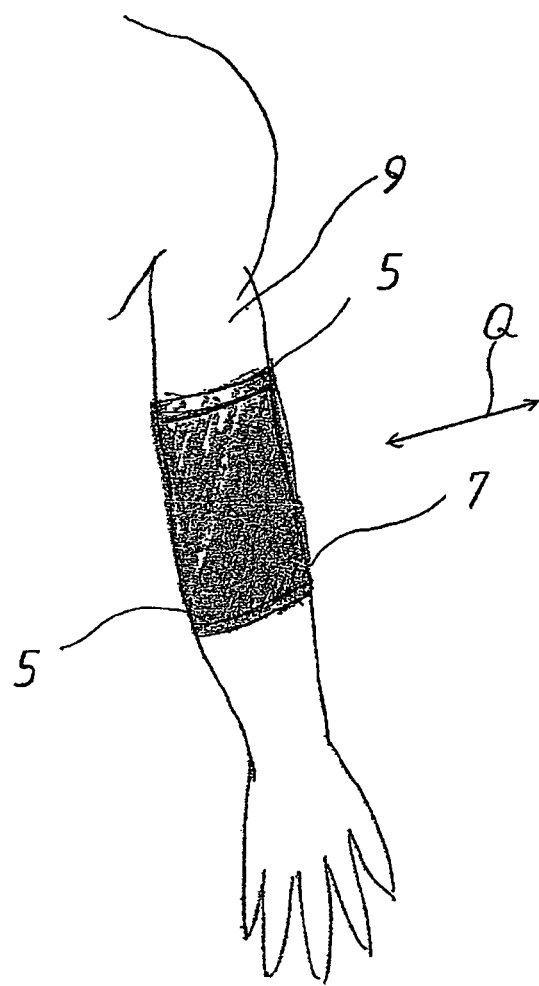
FIG. 7 shows a schematic view of a human arm with an arm sleeve according to the present invention.

In FIG. 7 the piece of clothing according to the present invention is executed as an elbow sleeve 7. Hereby, the base material, which is available in form of dressing strips, can be tailored into a tubular structure without any modification. The lateral threads 5 shown in FIG. 7 are located at the rim. Due to the fabric structure of base material 1, elbow sleeve 7 adapts the shape of arm 9, which is achieved by the high extensibility in lateral direction Q.

Figure 8:
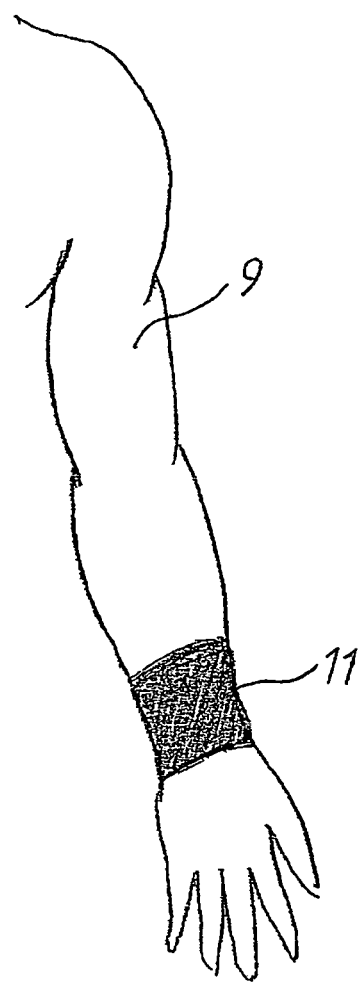
FIG. 8 shows a schematic view of a body part with an arm joint sleeve.

In FIG. 8 the base material according to the present invention is tailored into a sleeve 11 for the wrist of an arm 9. The wrist sleeve 11 adapts the shape of arm 9 due to the elastic extensibility in lateral direction Q as well.

Figure 9:
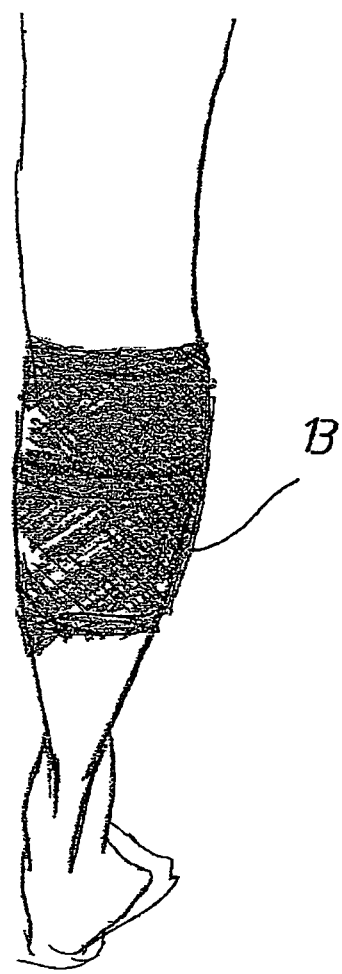
FIG. 9 shows a schematic view of a leg with a calf sleeve according to the present invention.

The piece of clothing according to the present invention shown in FIG. 9 is a calf sleeve 13, which is sewed from two, sewed up dressing base materials according to FIG. 1 to form a tubular structure.

Figure 10:
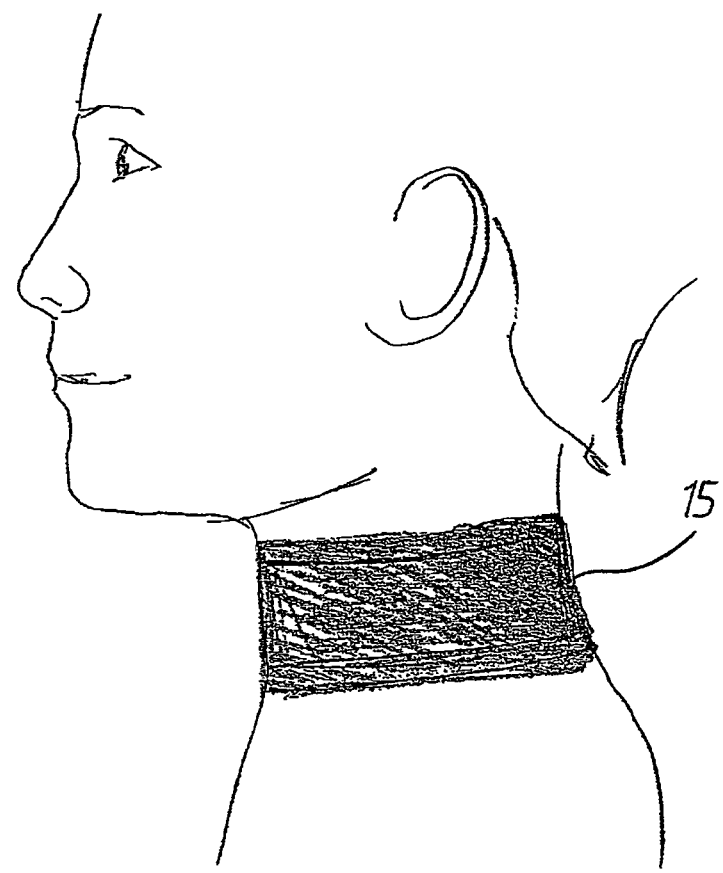
FIG. 10 shows a schematic view of a head with a neckband according to the present invention.

In FIG. 10 the piece of clothing according to the present invention is executed as a neckband 15.

Figure 11:
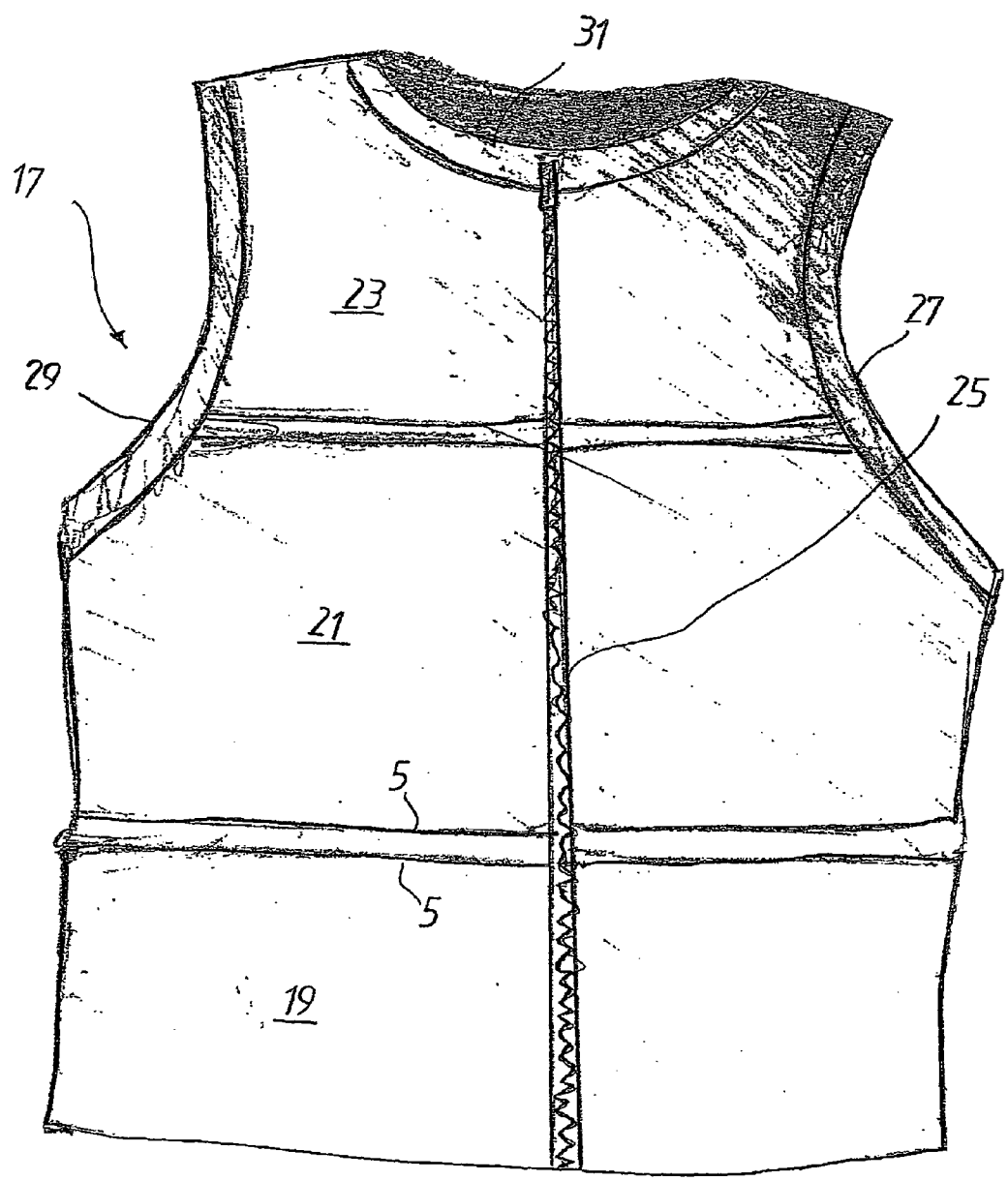
FIG. 11 shows a schematic view of a vest according to the present invention.

In FIG. 11 the piece of clothing according to the present invention is executed as a vest 17, which is formed essentially from two parallely aligned dressing base materials 19, 21, 23. Said dressing base materials 19, 21, 23 are connected with each other via their adjoining longitudinal rims. The vest 17 comprises a zipper 25 in its center. The vest 17 is provided with openings for the arms 27 and for the neck 31. Two opposing lateral threads 5 are visible at the sewed rims.

Figure 12:
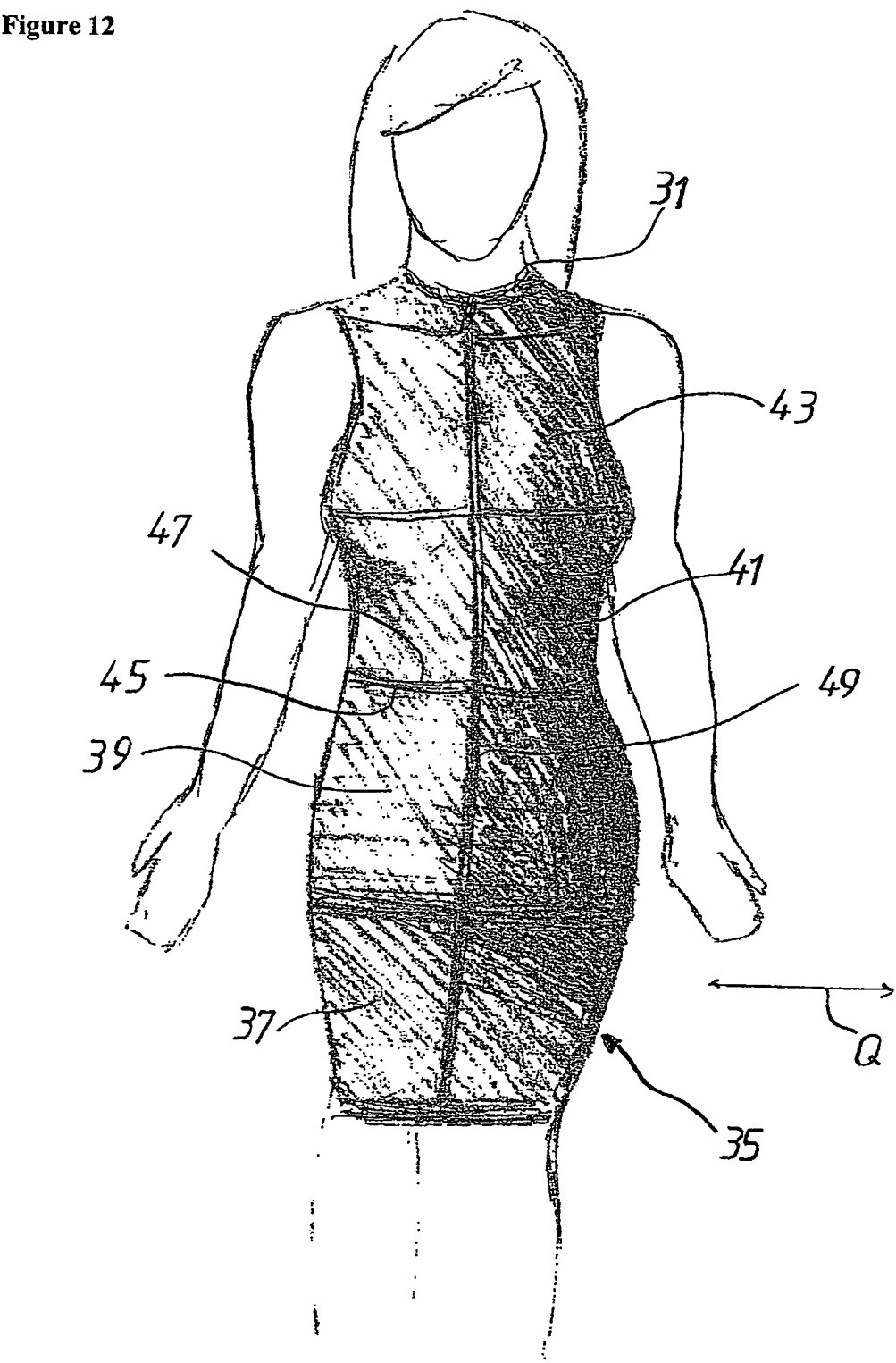
FIG. 12 shows a schematic view of a female person carrying a short dress according to the present invention.

The piece of clothing shown in FIG. 7 is a short dress 35 tailored from the dressing material according to FIG. 1, which is formed by at least four strips 37, 39, 41, and 43 of the dressing base material. Strips 37, 39, 41, and 43 are connected via seams, wherein the two lateral threads 45, 47 are indicated in FIG. 12. The short dress 35 covers the upper part of the body as well as the waist and abdomen, wherein dress 35 adapts the shape of the body due to its elastic extensibility in later direction Q. In its center the dress 35 has a zipper 49 extending from the neck opening 31 to the lower end.

Figure 13:
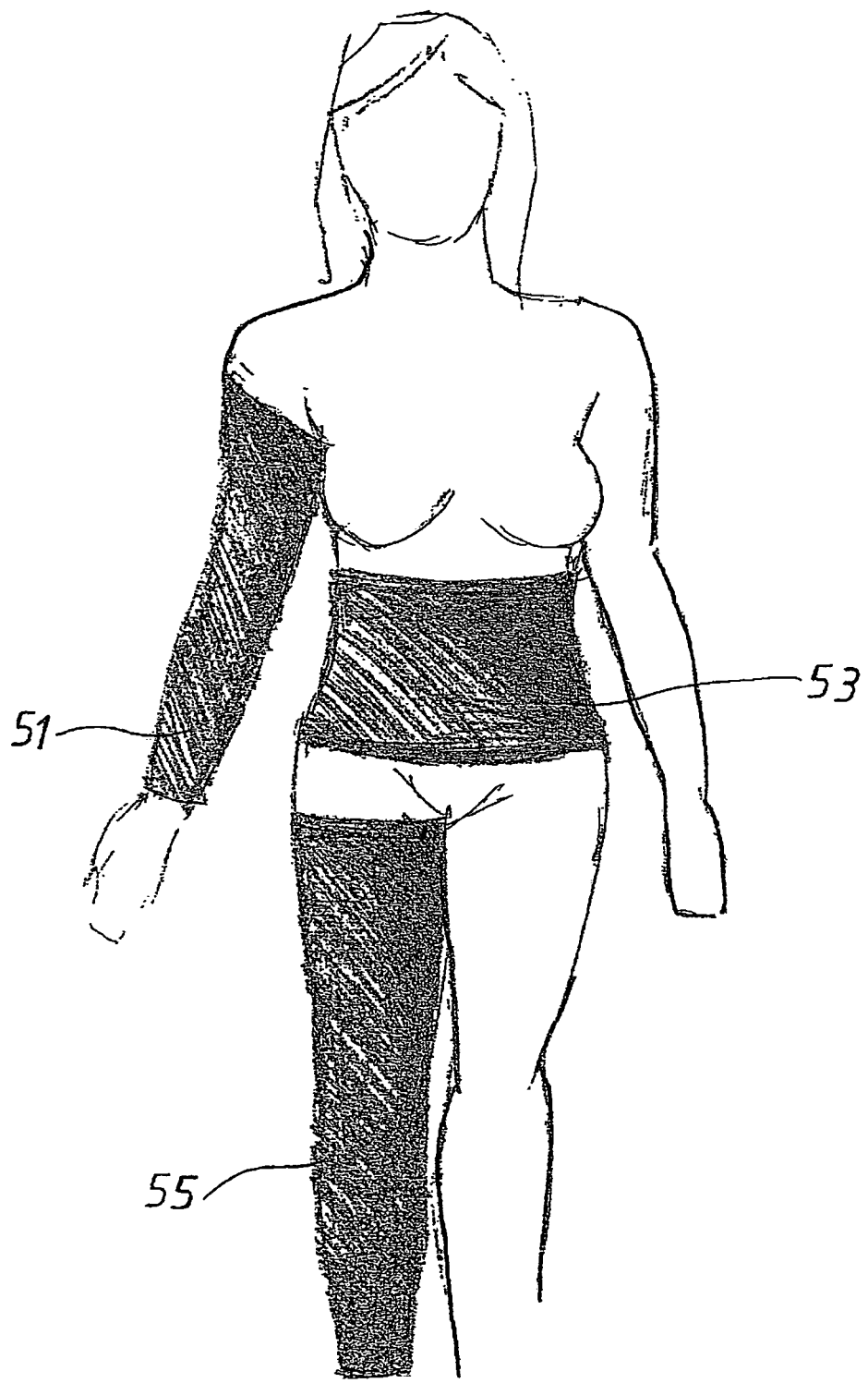
FIG. 13 shows a schematic view of a female person carrying an assembly of an arm sleeve, an abdominal sleeve and a leg sleeve.

In FIG. 13 an assembly of three pieces of clothing according to the present invention is shown, namely an arm sleeve 51, an abdominal sleeve 53 and a leg sleeve 55.

Figure 14:
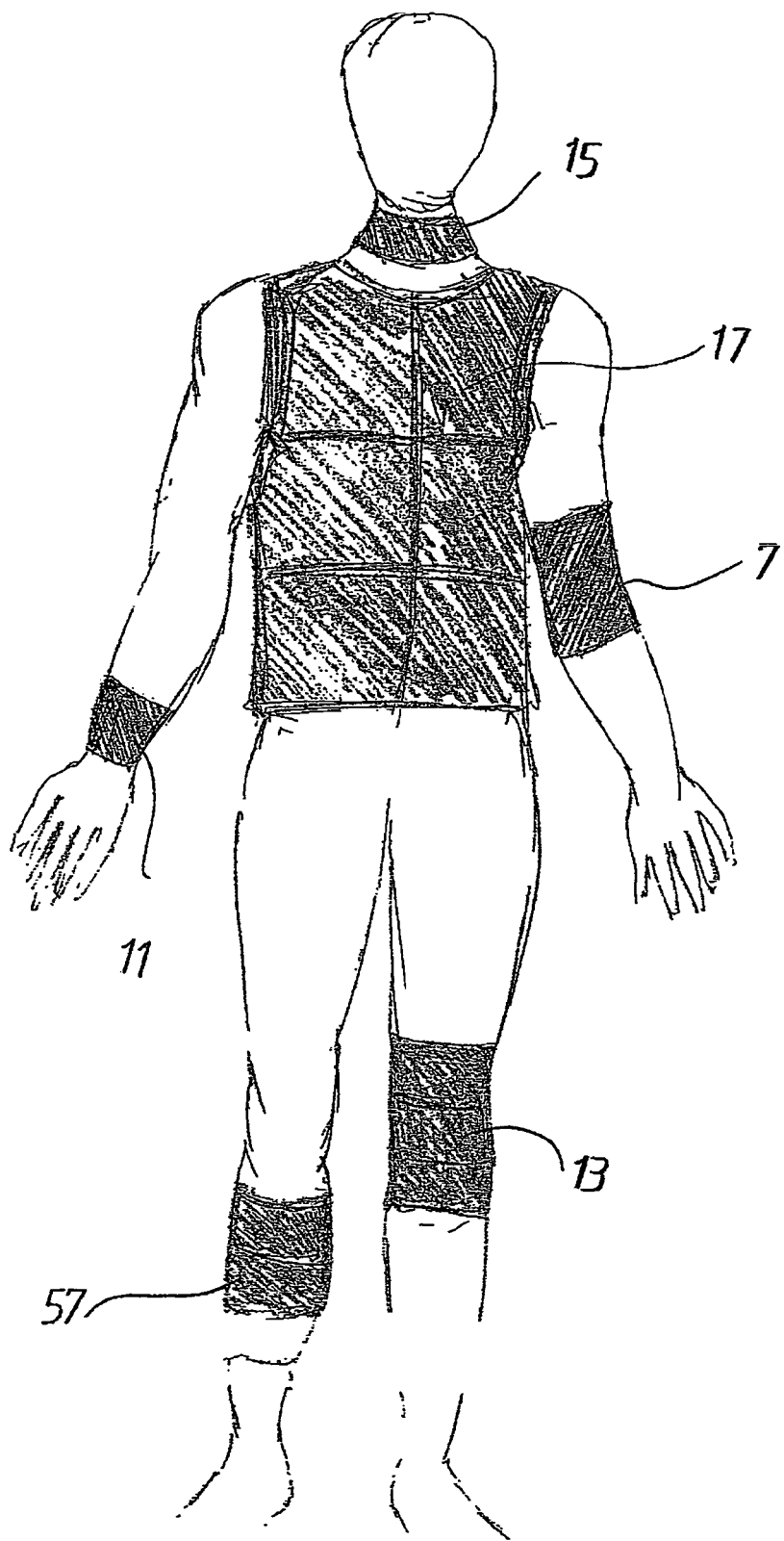
FIG. 14 shows a schematic view of a male person carrying an assembly of an arm joint sleeve according to the present invention, an elbow joint sleeve, a vest, a neckband, knee sleeve, and a calf sleeve.

FIG. 14 shows an assembly of six pieces of clothing, namely a vest 17, a neckband 15, a calf sleeve 13, a wrist sleeve 11, an elbow sleeve 7, and a calf sleeve 57.

With respect to all figures it has to be noted that using an exogenous liquid medium according to the present invention, namely a liquid containing alcohol and caffeine, will result in significant performance-enhancing effects, if the piece of clothing is worn in the positions shown in the figures. Surprisingly, also enhanced metabolic activities have been demonstrated in those regions, in which the piece of clothing according to the present invention had been soaked with said liquid medium.

Preferably, said liquid medium comprises about 15% alcohol, about 84% water, about 0.2% menthol and 0.2% camphor, about 0.2% coenzyme A, about 0.2% carnitine and about 0.2% caffeine.

The features disclosed in the above description, the figures, and the claims can be of importance for the realization of the invention in various embodiments both by themselves and in their arbitrary combination.

In order that the invention may be more fully understood, the following example is provided. It should be understood that these examples are for illustrative purposes only, and are not to be construed as limiting the invention in any way.

EXAMPLES

Example 1

Treatments have are performed on a female subject, twice per week, for 5 weeks (see FIG. 1). As baseline data, measurements at this time point included body weight.

In each skin cooling treatment, portions of the subject's body are wrapped in elastic bandages soaked with an aqueous alcohol solution consisting of (by weight) about 8% ethanol, 7% isopropanol, about 83.6% water; about 0.9% cetiol; about 0.13% menthol; about 0.13%, about 0.1% caffeine, about 0.1% coenzyme A, and about 0.1% carnitine. For female subjects, the breasts are not wrapped, so they are not subjected to the skin cooling treatment. During each skin cooling treatment, the patients remain in a supine position for 25 minutes. Evaporation of the cooling solution from the wet bandages lowers the skin temperature to approximately 24-25° C.

The result show a statistically significant reduction in weight, plus the data indicate a significant size reduction, which appears to result from loss of fat. Moreover, the data indicate a significant size reduction only in areas that were disproportionately large (relative to body symmetry), and only in areas that received the therapy. Thus, the results indicate localized fat reduction, i.e., "spot reduction." The overall weight was reduced from 60 kg at the beginning of the treatment to about 57 kg after 5 weeks, without that the patient had to follow a particular diet. In contrast, the regular diet led to an actual increase of the body weight, once the diet was ceased.

Example 2

This example shows comparative studies between the inventive preferred composition "Liquid Ice™" (the same composition as in example 1 was used), versus regular water-based ice.

1. Subject Data

N=24 healthy subjects; N=17 female, N=7 male

| Descriptive Statistics | | | | | |
|---|---|---|---|---|---|
| | N | Minimum | Maximum | Mean | Std. Deviation |
| age | 24 | 21.00 | 37.00 | 24.5000 | 4.18070 |
| htmeters | 24 | 1.52 | 2.06 | 1.6965 | .12358 |
| wtkg | 24 | 46.82 | 100.00 | 71.9508 | 16.72658 |
| txskfld | 24 | 3.00 | 13.00 | 6.7500 | 3.07868 |
| ctskfld | 24 | 3.00 | 13.00 | 6.8750 | 3.08661 |
| Valid N (listwise) | 24 | | | | |

Txskfld: Treatment knee skin fold thickness (mm)
Ctskfld: Control knee skin fold thickness (mm)

2. Environment:

a) Mean room temperature 25.2±0.2° C. (p>0.05, no difference between test days)

3. Skin Temperature (see FIG. 3)

Assessed with 2 (time, before and after)×2 (condition, treatment and control) ANOVA with gender and group (ice and Liquid Ice™) as between-subjects factors. The main effects of time and condition were significant ($p<0.001$). Additionally, the interactions of time and group; condition and group; time and condition; and time, condition, and group were significant ($p<0.001$).

Descriptive Statistics

|  | gender | group | Mean | Std. Deviation | N |
|---|---|---|---|---|---|
| txskn0 | 1 | 1 | 30.3120 | .86736 | 5 |
|  |  | 2 | 30.6650 | .13435 | 2 |
|  |  | Total | 30.4129 | .73091 | 7 |
|  | 2 | 1 | 30.2843 | 1.65837 | 7 |
|  |  | 2 | 30.4050 | .96313 | 10 |
|  |  | Total | 30.3553 | 1.24774 | 17 |
|  | Total | 1 | 30.2958 | 1.33187 | 12 |
|  |  | 2 | 30.4483 | .87798 | 12 |
|  |  | Total | 30.3721 | 1.10594 | 24 |
| ctskn0 | 1 | 1 | 30.3480 | .67192 | 5 |
|  |  | 2 | 30.4100 | .11314 | 2 |
|  |  | Total | 30.3657 | .55139 | 7 |
|  | 2 | 1 | 30.2786 | 1.67609 | 7 |
|  |  | 2 | 30.3470 | 1.33693 | 10 |
|  |  | Total | 30.3188 | 1.43530 | 17 |
|  | Total | 1 | 30.3075 | 1.30299 | 12 |
|  |  | 2 | 30.3575 | 1.21003 | 12 |
|  |  | Total | 30.3325 | 1.23000 | 24 |
| txskn30 | 1 | 1 | 14.6780 | .94579 | 5 |
|  |  | 2 | 25.4900 | 1.82434 | 2 |
|  |  | Total | 17.7671 | 5.38370 | 7 |
|  | 2 | 1 | 13.5229 | 1.56462 | 7 |
|  |  | 2 | 24.6090 | .91532 | 10 |
|  |  | Total | 20.0441 | 5.74618 | 17 |
|  | Total | 1 | 14.0042 | 1.41929 | 12 |
|  |  | 2 | 24.7558 | 1.05150 | 12 |
|  |  | Total | 19.3800 | 5.62568 | 24 |
| ctskn30 | 1 | 1 | 31.2000 | .50759 | 5 |
|  |  | 2 | 31.6950 | .07778 | 2 |
|  |  | Total | 31.3414 | .48074 | 7 |
|  | 2 | 1 | 31.1829 | .85305 | 7 |
|  |  | 2 | 31.2990 | .79279 | 10 |
|  |  | Total | 31.2512 | .79366 | 17 |
|  | Total | 1 | 31.1900 | .70049 | 12 |
|  |  | 2 | 31.3650 | .73386 | 12 |
|  |  | Total | 31.2775 | .70727 | 24 |

Gender; 1 = male, 2 = female
Group; 1 = Ice, 2 = Liquid Ice ™
txskn0: Treatment skin temperature at time 0 (° C.)
ctskn0: Control skin temperature at time 0 (° C.)
txskn30: Treatment skin temperature after 30 minutes (° C.)
ctskn30: Control skin temperature after 30 minutes (° C.)

Figure 3:
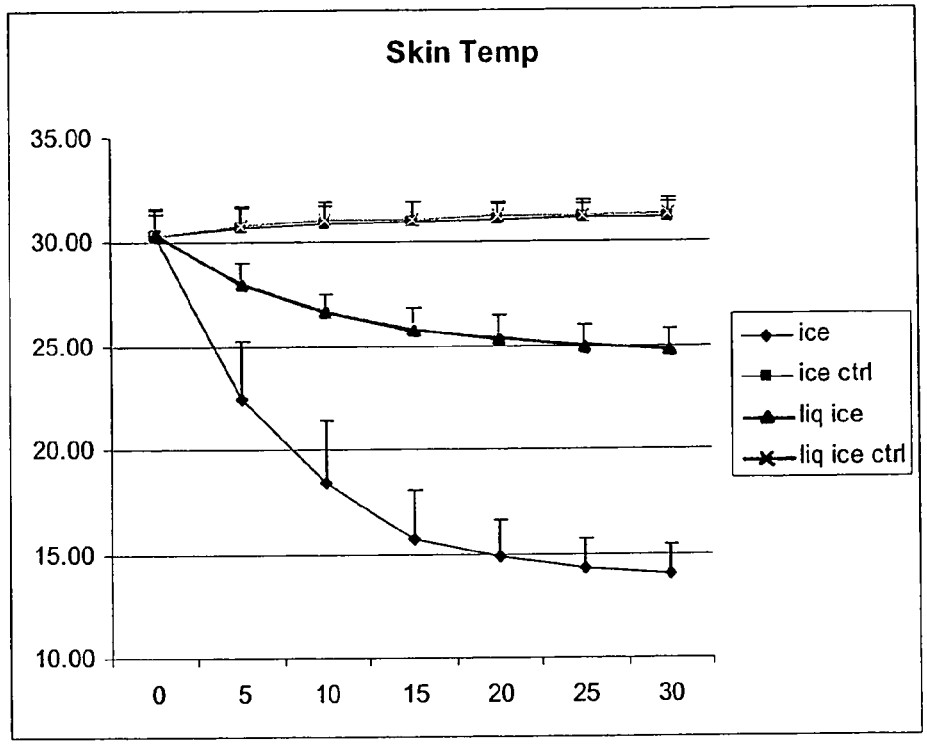
FIG. 3 shows a schematic diagram of the skin temperature according to example 2.
Figure 4:
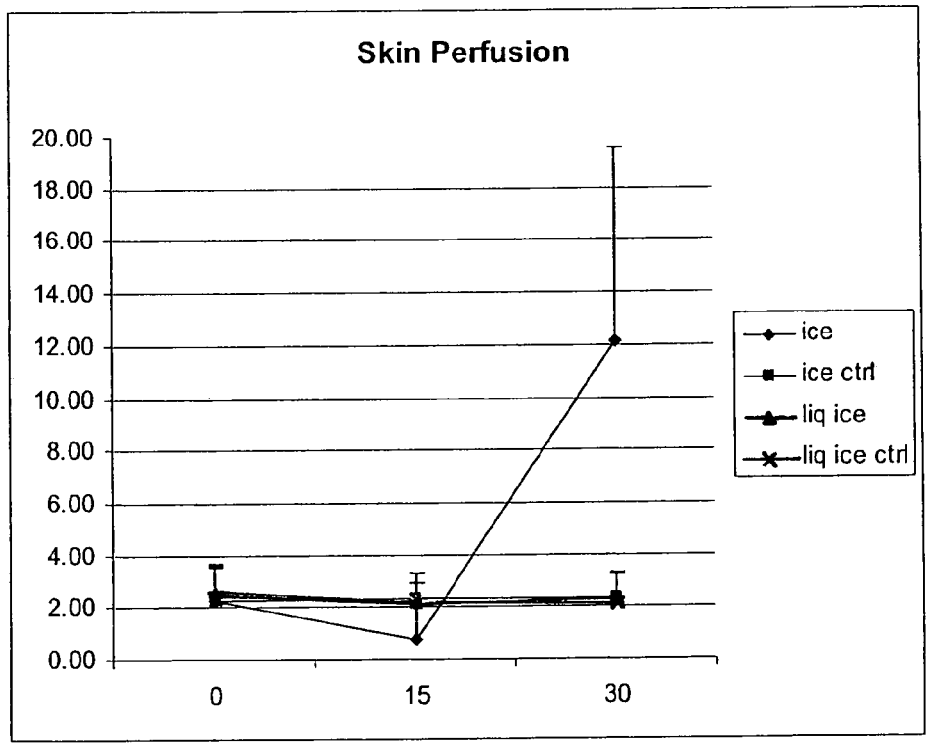
FIG. 4 shows a schematic diagram of the skin perfusion according to example 2.
Figure 5:
FIG. 5 show pictures of a test person before (A), and after (B) a 14 day period including 10 treatments at home. The person lost an overall body mass of 3.6 kg, apparently exclusively on the stomach/abdomen, where the treatment was applied using a wrap. No specific diet was followed during the treatment.
Figure 5:
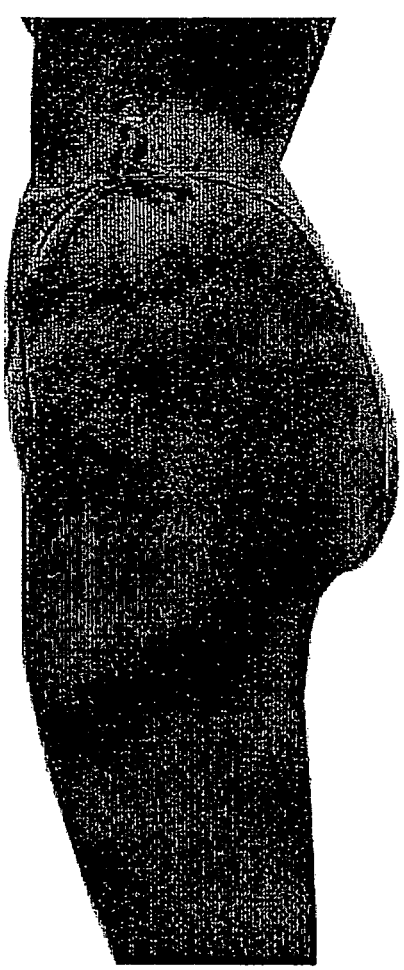

The main effects and interactions point to a difference between pre and post treatment times that existed between ice and Liquid Ice™ applications and that both treatments (ice and Liquid Ice™) were each significantly different from the control limbs. FIG. 3 is a graph of the data:

4. Skin Perfusion:

The skin perfusion was assessed with a 3 (time; before, 15 minutes, and after 30 minutes)×2 (condition, treatment and control) ANOVA with gender and group (ice and Liquid Ice™) as between-subjects factors. In this experiment, a difference occurred at time 15 and time 30 between ice and Liquid Ice™ and the control conditions (FIG. 4).

It can be seen from the data that water-based ice rapidly cools down the skin, leading to a stop of the blood flow through the skin. Thus, the metabolism in the skin is halted. After a certain time, the skin perfusion drastically increases, in order to re-warm the frozen skin. The Liquid Ice™ formulation only leads to a slight and constant decrease of the skin temperature, thus, the metabolism is advantageously activated, in contrast to a stop ("frozen") in the case of ice.

Other embodiments are within the following claims.

The invention claimed is:

1. A method for controlled lowering of skin temperature of a human subject and for actively stimulating fat metabolism, comprising contacting a composition with a region of the skin of the subject for 10 to 240 minutes, wherein the composition comprises,
   between 5 to 15% alcohol,
   between 80 to 95% water,
   between 0.1 to 2% menthol and/or camphor,
   0.1 to 2% coenzyme A,
   between 0.1 to 2% carnitine, and
   between 0.1 to 2% caffeine,
   thereby cooling the skin and actively stimulating fat metabolism.

2. The method according to claim 1, wherein the composition is contacted with the skin for 10-40 minutes.

3. The method according to claim 1, wherein the composition is contacted with the region of the skin by a woven or nonwoven fabric wrap.

4. The method according to claim 3, wherein the fabric wrap is an elastic cotton crepe bandage or vest.

5. The method according to claim 1, wherein the controlled reduction of skin temperature in the region of skin contacted with the composition is a reduction of 3° C. to 12° C.

6. The method according to claim 5, wherein the controlled reduction of skin temperature in the region of skin contacted with the cooling solution is a reduction of about 6° C.

7. The method, according to claim 1, used as part of a cosmetic treatment.

8. The method, according to claim 7, wherein the cosmetic treatment is against local body fat.

9. The method, according to claim 1, used for preventing or reducing systemic and/or local body fat.

10. The method for preventing or treating systemic and/or local obesity.

11. The method, according to claim 1, used for preventing or treating obesity and obesity related diseases.

12. The method according to claim 1, wherein said treatment is for a pediatric form.

13. The method according to claim 1, wherein the alcohol is selected from ethanol, isopropanol, or a mixture thereof.

* * * * *